United States Patent [19]

Vora

[11] 4,172,209

[45] Oct. 23, 1979

[54] PROCESS FOR PRODUCING DICARBOXYLIC ACIDS BY THE OXIDATION OF XYLENE

[75] Inventor: Bipin V. Vora, Elk Grove Village, Ill.

[73] Assignee: UOP Inc., Des Plaines, Ill.

[21] Appl. No.: 936,317

[22] Filed: Aug. 23, 1978

[51] Int. Cl.$^2$ ............................................. C07C 51/33
[52] U.S. Cl. .................................................... 562/414
[58] Field of Search ........................................ 562/414

[56] References Cited

U.S. PATENT DOCUMENTS 3,089,906  5/1963  Saffer et al. ........................... 562/414

*Primary Examiner*—A. Siegel
*Attorney, Agent, or Firm*—James R. Hoatson, Jr.; John F. Spears, Jr.; William H. Page, II

[57] ABSTRACT

A process for the catalytic liquid-phase oxidation of xylenes to produce benzene dicarboxylic acids. An off-gas stream which remains after a partial condensation of the oxidation zone vapor-phase effluent stream and the off-gas streams of an acetic acid fractionation column and a methyl acetate fractionation column are scrubbed by internally generated water streams. The aqueous scrubbing liquids are then processed in fractionation columns used in the process to recover acetic acid and methyl acetate.

4 Claims, 1 Drawing Figure

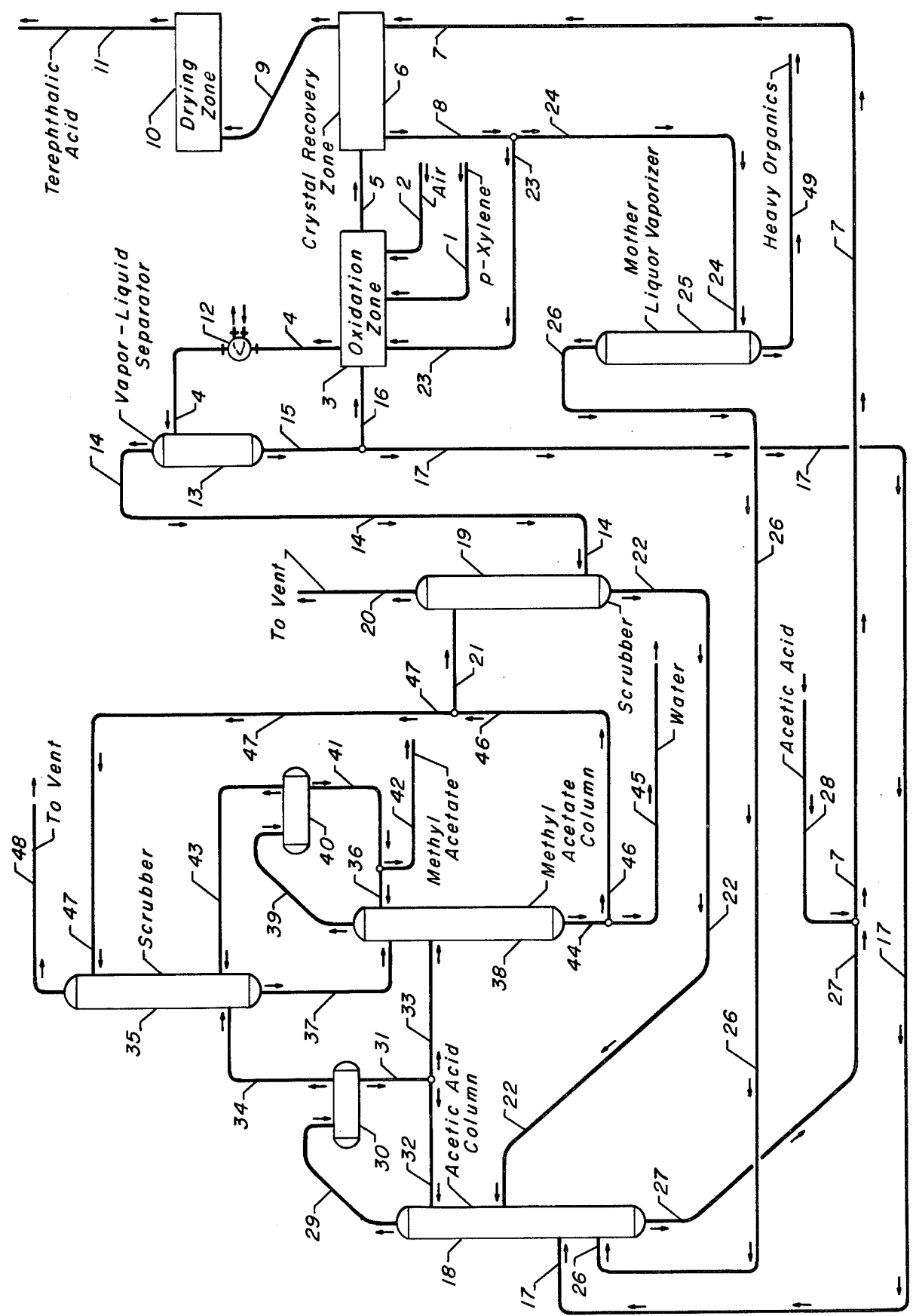

PROCESS FOR PRODUCING DICARBOXYLIC ACIDS BY THE OXIDATION OF XYLENE

FIELD OF THE INVENTION

The invention generally relates to the oxidation of aromatic hydrocarbons to the corresponding aromatic carboxylic acid. The invention more specifically relates to a continuous process for the production of benzene dicarboxylic acids, such as phthalic acid or terephthalic acid, by the catalytic liquid-phase oxidation of the corresponding xylene isomer in the presence of a solvent such as acetic acid. The invention also relates to the removal of vaporous hydrocarbons from the off-gas streams of such a process in order to recover the hydrocarbons and to minimize the pollution problems associated with the release of the off-gas streams into the atmosphere.

PRIOR ART

Large amounts of benzene dicarboxylic acids are produced commercially by the oxidation of the various xylene isomers. Several different oxidation processes are known, with examples set forth in Volume 15 of Kirk & Othmer's *Encyclopedia of Chemical Technology*, Interscience Publishers, (1968). Specific references on the subject include U.S. Pat. Nos. 2,833,816 (Cl. 260-524); 2,964,559 (Cl. 260-525); 3,089,906; 3,089,907; 3,996,271 and 4,051,178 (all Cl. 260-524) and 4,053,506 (Cl. 260-525). Typical reactions conditions, catalysts and operating procedures are set out in these references.

The use of a water washing step to remove acetic acid from the off-gas of a xylene oxidation zone is known and is shown in U.S. Pat. Nos. 2,962,361 (Cl. 23-260) and 3,170,768 (Cl. 23-263). U.S. Pat. No. 3,370,400 (Cl. 55-73) describes the application of water washing to the removal of 1,4-naphthoquinone from the waste gases of a naphthalene oxidation process. However, this reference also describes the drawbacks of this method of gas purification and refers to the purification of the used washing water as an indispensable second step.

BRIEF SUMMARY OF THE INVENTION

The invention provides a process for the production of a benzene dicarboxylic acid by the liquid-phase oxidation of a xylene in the presence of a solvent comprising acetic acid. Both the by-product methyl acetate and acetic acid solvent are recovered from the net off-gas streams of the fractionation columns and the oxidation zone used in the process by scrubbing the off-gas streams with water, which is then purified in one of the fractionation columns. The recovery of the water, methyl acetate and acetic acid and the off-gas scrubbing steps are integrated with the separation and recovery of the water and methyl acetate produced in the xylene oxidation steps.

The invention may be broadly characterized as a process for the production of a benzene dicarboxylic acid by the oxidation of a xylene which comprises the steps of passing a feed stream comprising xylene, hereinafter described first and second recycle liquid streams and a first vapor stream comprising oxygen or air into an oxidation zone and effecting the oxidation of xylene and the production of a liquid-phase oxidation zone effluent stream comprising a benzene dicarboxylic acid, acetic acid, dissolved catalysts and oxidation zone by-products and a vapor-phase oxidation zone effluent stream comprising acetic acid, methyl acetate, nitrogen and excess oxygen; passing the liquid-phase oxidation zone effluent stream into a crystal recovery zone wherein crystals of the benzene dicarboxylic acid are recovered from the liquid-phase oxidation zone effluent stream and the crystals are then contacted with a washing liquid stream comprising acetic acid to produce a mother liquid stream comprising acetic acid, water, dissolved catalysts and hydrocarbonaceous oxidation zone by-products and a crystal stream comprising benzene dicarboxylic acid crystals; passing the crystal stream through a drying zone to produce a product stream of benzene dicarboxylic acid; returning at least a first portion of the mother liquor stream to the oxidation zone as the first recycle liquid stream; partially condensing the vapor phase oxidation zone effluent stream and then separating the resultant liquid and vapor phases into a condensate liquid stream comprising water, methyl acetate and acetic acid and an oxidation zone off-gas stream comprising acetic acid, nitrogen, oxygen, carbon dioxide, carbon monoxide and methyl acetate; returning a first portion of the condensate liquid stream to the oxidation zone as the second liquid recycle stream and passing a second portion of the condensate liquid stream into an acetic acid fractionation zone; passing at least a portion of the bottoms liquid stream of the acetic acid fractionation zone into the crystal recovery zone as the washing liquid stream; passing the oxidation zone off-gas stream into a first scrubbing zone and contacting the oxidation zone off-gas stream with a first water stream to produce a vent gas stream comprising nitrogen, oxygen, carbon dioxide and carbon monoxide and a first scrubbing zone liquid stream comprising water, methyl acetate and acetic acid; passing the first scrubbing zone liquid stream into the acetic acid fractionation zone; transferring a net overhead liquid stream comprising water and methyl acetate from the acetic acid fractionation zone to a methyl acetate fractionation zone; withdrawing a net overhead liquid stream comprising methyl acetate from the methyl acetate fractionation zone; contacting a net vapor stream comprising nitrogen and other gases and methyl acetate removed from the acetic acid fractionation zone and a net vapor stream comprising nitrogen and methyl acetate removed from the methyl acetate fractionation zone with a second water stream in a second scrubbing zone and thereby forming a second vent gas stream and a second scrubbing zone liquid stream comprising water and methyl acetate; passing the second scrubbing zone liquid stream into the methyl acetate fractionation zone; passing a first portion of a net bottoms liquid stream formed in the methyl acetate fractionation zone into the first scrubbing zone as the first water stream and passing a second portion of the bottoms liquid stream of the methyl acetate fractionation zone into the second scrubbing zone as the second water stream.

DESCRIPTION OF THE DRAWING

The Drawing illustrates the preferred embodiment of the invention. For clarity in describing the inventive concept, various subsystems and apparatus associated with the operation of the process have not been shown. These items include flow and pressure control valves, pumps, temperature and pressure monitoring systems, reactor and fractionator internals, etc., which may be of customary design. This representation of the preferred embodiment is not intended to preclude from the scope of the inventive concept those other embodiments set out herein or which are the result of reasonable and normal modification of these embodiments.

Referring now to the Drawing, a feed stream comprising para-xylene enters the process through line 1 and is directed into a liquid-phase catalytic oxidation zone 3 wherein it is admixed with a first vapor stream comprising air from line 2 and recycle liquid streams from lines 16 and 23. The oxidation zone is maintained at oxidation-promoting conditions which effect the oxidation of the great majority of the p-xylene to terephthalic acid, but which also produces a number of by-products.

The nitrogen which enters the oxidation zone in the first vapor stream as a component of the air fed to the oxidation zone is removed from the oxidation zone through line 4 as a component of a vapor-phase oxidation zone effluent stream. This vapor stream will also contain any excess oxygen which has not been consumed in the oxidation zone and an equilibrium amount of the more volatile hydrocarbons present in the oxidation zone including p-xylene, acetic acid and methyl acetate. The vapor-phase oxidation zone effluent stream is passed through a condenser 12 and into a vapor-liquid separator 13. The condensate collected in the separator is withdrawn through line 15 and divided into a first portion which is returned to the oxidation zone as a recycle liquid stream in line 16 and a second portion which is passed through line 17 to the acetic acid fractionation column 18.

A liquid-phase oxidation zone effluent stream is passed into a crystal recovery zone 6 through line 5. The crystal recovery zone preferably comprises two centrifuges and an intermediate reslurrying tank. The solid crystals of terephthalic acid move through crystal recovery zone in a basically countercurrent manner to a washing liquid stream which enters the crystal recovery zone through line 7. The admixture of the washing liquid stream with the liquid which separates from the liquid-phase oxidation zone effluent stream in the centrifuges forms a mother liquor stream. The mother liquor stream exits the crystal recovery zone carrying the impurities removed from the terephthalic acid crystals and components of the homogeneous catalyst. The mother liquor stream is carried by line 8 and may be divided into a first portion which is passed into the oxidation zone as a recycle liquid stream through line 23 and a second portion which is passed into a mother liquor vaporizer 25 through line 24. The terephthalic acid crystals are removed from the crystal recovery zone in line 9 as a crystal stream and are passed through a drying zone 10 wherein acetic acid is removed by contacting the crystals with a stream of hot inert gas. A product stream of terephthalic acid is removed from the process through line 11.

When a portion of the mother liquor stream is passed into the vaporizer 25, a major part of this stream is vaporized to form a vaporizer off-gas stream removed through line 26 and passed into the acetic acid column 18. The remaining liquid material is removed from the vaporizer through line 49 and comprises various heavy organic by-products produced in the oxidation zone.

The uncondensed portion of the vapor-phase oxidation zone effluent stream which is removed from the vapor-liquid separator 13 in line 14 is passed into a lower locus of a first scrubbing tower or scrubber 19. This vapor stream is therein contacted with a first water stream which enters an upper portion of the scrubber through line 21. The scrubber is operated at conditions which effect the transfer of essentially all of the acetic acid and methyl acetate present in the vapor stream to the liquid-phase water stream. There is thereby formed a vent gas stream removed in line 20 which comprises nitrogen, excess oxygen and other gases but which has a very low concentration of acetic acid. Also formed is a first scrubbing zone liquid stream removed in line 22. This first scrubbing zone liquid stream is passed into the acetic acid fractionation column 18.

The acetic acid fractionation column 18 is operated under conditions effective to separate the entering streams into an overhead vapor stream comprising water and methyl acetate removed in line 29 and a first bottoms liquid stream of relatively pure acetic acid which is removed in line 27. A make-up stream of acetic acid from line 28 is admixed with the bottoms liquid stream of the acetic acid fractionation column to form the washing liquid stream passed into the crystal recovery zone via line 7.

The overhead vapor stream of the acetic acid column is passed through an overhead condenser not shown and then into a first overhead receiver 30. A liquid collected in this overhead receiver is withdrawn through line 31 and divided into a first portion returned to the acetic column through line 32 as reflux liquid and a second portion which is passed into a methyl acetate column 38 through line 33 as the net overhead of the acetic acid column. A small nitrogen bleed is passed into the first overhead receiver from a source not shown. This nitrogen and other noncondensable materials which also enter the overhead receiver are removed as a vapor stream through line 34 and are passed into a second scrubber 35.

The methyl acetate column 38 is operated under conditions effective to separate the entering liquid stream into an overhead vapor stream comprising methyl acetate which is removed in line 39 and a bottoms liquid stream consisting essentially of water. The overhead vapor stream of the methyl acetate column is passed through a condenser not shown and into a second overhead receiver 40. The overhead liquid which is collected in this receiver is withdrawn through line 41 and divided into a first portion which is passed into the methyl acetate column as reflux liquid through line 36 and a second portion which is removed as a net methyl acetate product stream through line 42. In a manner similar to the overhead receiver of the acetic acid column, a small stream of nitrogen is passed into the overhead receiver of the methyl acetate column for purposes of pressure control. This nitrogen and any methyl acetate which is vaporized by its presence and any other uncondensed gases or hydrocarbons are passed from the second overhead receiver to the bottom of the second scrubber through line 43.

The aqueous bottoms liquid stream of the methyl acetate column is removed in line 44 and is then divided into a first portion which is removed from the process as a product stream through line 45 and a second portion carried by line 46. The liquid flowing through line 46 is again divided into the portion passed into the first scrubber 19 through line 21 and the remaining portion which is passed into an upper portion of the second scrubber 35 through line 47.

The second scrubber is operated at conditions effective to cause the transfer of acetic acid and methyl acetate to the entering scrubbing water from the vapor stream. There is thereby produced a second vent gas stream comprising nitrogen and removed in line 48 and a second scrubbing zone liquid stream which comprises water and methyl acetate and which is carried from this scrubber in line 37. The second scrubbing zone liquid stream is passed into the methyl acetate column to effect the recovery of water and methyl acetate.

DETAILED DESCRIPTION

The oxidation of aromatic hydrocarbons such as toluene, xylenes and naphthalene to produce the corresponding carboxylic acids is an important chemical process which is performed commercially. For instance, benzene polycarboxylic acids are produced in this manner and used as organic building blocks for plasticizers, alkyd resins and condensation polymers, with the polyesters and polyamides being the most common of the polymers. Of the polydicarboxylic acids, the dicarboxylic acids have the greatest commercial usage. Phthalic acid (o-benzene dicarboxylic acid) and terephthalic acid (p-benzene dicarboxylic acid) are often converted to phthalic anhydride and dimethyl terephthalate respectively.

The oxygen consumed in the oxidation reaction may be supplied in the form of pure oxygen, but is commonly supplied by passing compressed air into the reaction zone. The large volume of nitrogen contained in the air is not consumed in the oxidation reaction and therefore must be vented from the reaction zone. This produces a relatively warm vapor-phase reaction zone effluent stream comprising a mixture of all of the easily vaporized hydrocarbons present in the reaction zone. This vapor stream is normally cooled to effect the condensation and recovery of some of these hydrocarbons. However, the constraints on condensation imposed by the minimum practical temperature of the coolant utilized to perform the condensation and the large volume of vapor to be handled in this operation result in a large amount of hydrocarbons remaining as an off-gas stream after the condensation.

To prevent the loss of these valuable hydrocarbons when the oxidation zone off-gas stream is discharged into the atmosphere and to prevent pollution of the atmosphere, the vapor stream is scrubbed with a liquid capable of adsorbing at least the predominant hydrocarbons. According to the preferred mode of operation, the vapor stream contains acetic acid and methyl acetate which is a by-product of the oxidation process. Water is the preferred adsorbent liquid. The hydrocarbon-containing water must in turn be processed for the removal and recovery of the acetic acid and methyl acetate before it may be reused in the scrubbing zone or discharged from the process.

Also according to the preferred mode of operation, acetic acid is utilized as both a solvent for the oxidation reaction and as a washing liquid in the purification of the product carboxylic acid. It is necessary to use a relatively high purity stream of acetic acid as the washing liquid. This requires the separation by fractionation of the recycled acetic acid from methyl acetate and water, which are by-products of the oxidation reaction. The methyl acetate is recovered from the overhead of the acetic acid in a second fractionation zone and may be sold as a valuable product.

It will normally be necessary to vent a vapor stream comprising inert gases such as carbon dioxide, nitrogen and carbon monoxide from the fractionation zone in which the acetic acid is purified. These gases are dissolved in the various liquid streams fed to the acetic acid fractionation zone. In addition, for purposes of pressure control of the fractionation zones, it is desired to pass a small stream of nitrogen into the overhead receivers associated with both the acetic acid and methyl acetate fractionation zones. This results in the production of two net overhead gas streams comprising the nitrogen gas and other uncondensed materials present in the overhead receivers of these two fractionation zones. These gas streams serve as a medium for the discharge of additional amounts of acetic acid and/or methyl acetate. The vapor streams must therefore also be treated for the removal of vaporized hydrocarbons to lower discharges and recover valuable hydrocarbons.

It is an objective of the invention to provide an integrated process for the liquid-phase oxidation of aromatic hydrocarbons. It is a further objective of the invention to provide an integrated process for the production and purification of benzene polycarboxylic acids in which aromatic hydrocarbons are contacted with air at oxidation-promoting conditions and in which vaporized hydrocarbons are recovered from the off-gas streams of the process. It is yet another objective of the present invention to provide an integrated process for the production of high purity terephthalic acid from p-xylene in which acetic acid and methyl acetate are scrubbed from off-gas streams by contact with water which is reclaimed during the purification of acetic acid used as a washing liquid within the process.

The process may be performed in an apparatus of customary design similar to that used in other oxidation processes. Nevertheless, a brief description of some of the basic equipment used in the generically-labeled zones is included to insure a complete understanding of the inventive concept. The oxidation zone preferably comprises a vertical cylindrical vessel having separate inlets for air and for liquid hydrocarbons. The rate of liquid product withdrawal is controlled on the basis of the liquid level in the vessel. A vapor phase stream is removed from the top of the vessel.

Terephthalic acid is only sparingly soluble in the liquid mixture present in the reaction zone. It therefore tends to precipitate out as crystals in the reaction solution. To keep these crystals in suspension and also to provide a relatively uniform reactant concentration throughout the reaction zone, the reaction zone may be agitated by a rotating paddle-type mechanical mixer. Both the liquid reactants and the oxygen fed to the oxidation zone may enter at several locations to promote a uniform reactant distribution. The reaction zone may also comprise two or three reaction vessels with continuous countercurrent flow of the entering air and hydrocarbon streams as described in the previously referred to U.S. Pat. No. 2,962,361. The preferred catalyst-solvent system is corrosive to carbon steels, and a titanium-lined reaction vessel and similarly corrosion-resistant accessories should be used in those areas exposed to the catalyst system. Further details on reactor vessel construction are available in U.S. Pat. No. 3,130,015.

The liquid-phase reaction zone effluent stream contains crystals of crude carboxylic acid suspended in a liquid phase comprised of the solvent, any unconverted feed aromatic hydrocarbons, reaction by-products, the soluble quantity of carboxylic acid and components of the catalyst system. The liquid-phase reaction zone effluent is passed into the crystal recovery zone. Preferably, it is first subjected to a two-stage cooling operation and is then passed into a first filter or centrifuge wherein the crude carboxylic acid crystals are removed from the liquid. The liquid separated in this manner becomes a liquid stream customarily referred to as the mother liquor.

The mother liquor is collected for recycling as described herein and the wet crystals are passed into a first stirred slurrying drum. The wet crystals are slurried with a washing liquid in this drum to remove impurities which must be eliminated in order to comply with product specifications. These impurities are mainly oxidation products of the feed aromatic hydrocarbon. In the preferred case of p-xylene oxidation, the principal by-products are p-toluic acid, p-tolualdehyde, p-carboxybenzaldehye and benzoic acid. The washing liquid is typically the same as the solvent used in the oxidation zone and is preferably relatively impurity-free acetic acid. The slurrying of the carboxylic acid crystals tends to selectively dissolve sizable percentages of the impurities, which are more soluble in acetic acid than terephthalic acid.

The resulting crystal slurry is transferred to a second filter or centrifuge. The carboxylic acid crystals are again separated from the liquid-phase in which they are transported and are passed into a second stirred slurrying drum. Additional relatively high purity acetic acid is passed into this drum as washing liquid and an additional amount of impurities is removed from the carboxylic acid crystals. This second slurrying step may be deleted in those instances where it is not required to meet product specifications. The liquid withdrawn from the second centrifuge or filter may be used to form at least part of the washing liquid passed into the first slurrying drum.

The carboxylic acid crystals produced in this manner may be passed directly to an optional further purification step wherein they are heated to a relatively high temperature in admixture with relatively high purity acetic acid in a jacketed vessel. The liquid-phase acetic acid preferably contains some catalyst to aid in the oxidation of remaining impurities by oxygen charged to the bottom of the jacketed vessel. A stream of the material in the jacketed vessel is passed into the first of two crystallizers operated in series wherein crystals of high purity carboxylic acid are formed. The effluent of the second crystallizer is filtered and washed with more acetic acid washing liquid. The sequential use of a centrifuge and a slurrying drum is a conventional purification operation as is shown by the teachings of previously referred to U.S. Pat. No. 3,170,768. An alternative procedure is described in U.S. Pat. No. 4,053,506 (Cl. 260-525).

The wet crystals of product carboxylic acid are passed into a drying zone. This zone preferably comprises a very conventional dryer through which the crystals are slowly moved while evaporating acetic acid is swept from the dryer by a recirculated stream of nitrogen. The solid high purity carboxylic acid is then collected from the effluent of the drying zone.

The oxidation-promoting conditions maintained in the oxidation zone include a temperature within the broad range of 130° C. to 240° C. and preferably between 180° C. and 230° C. The oxidation-promoting conditions also include an elevated pressure as is necessary to maintain the bulk of the organic reactant and solvent in the liquid phase. The pressure may be in the broad range of from about 5.0 to about 25 kg/cm$^2$ (absolute). Preferably, the pressure is maintained between 9.0 and 14 kg/cm$^2$. Heat is removed from the oxidation zone by the partial evaporation of the solvent and water produced in the oxidation zone. The overall temperature of the oxidation zone may therefore be controlled by regulating the pressure within the oxidation zone.

The oxidation reaction is preferably effected in the presence of an aliphatic carboxylic acid used as solvent or reaction medium. Acetic acid is the preferred solvent. A molar excess of the solvent should be provided in the oxidation zone.

The subject process is applicable to the oxidation of a large number of aromatic hydrocarbons. A partial listing of the aromatic hydrocarbons which may be charged to the process and the corresponding carboxylic acid includes the following pairs of chemical compounds: methylbenzene and benzoic acid; 1,2-dimethylbenzene and phthalic acid; 1,3-dimethylbenzene and isophthalic acid; 1,4-dimethylbenzene and terephthalic acid; 1,2,3-trimethylbenzene and hemimellitic acid. Other aromatic hydrocarbons which may be charged to the process include 1,3,5-triisopropylbenzene and 1-methylnapthalene.

The preferred catalyst for use in the process comprises a catalytically effective amount of a bromine-promoted heavy metal oxidation catalyst. The heavy metal may be selected from the group consisting of manganese, cobalt, nickel, chromium, vanadium, molybdenum, iron, tungsten, tin or cerium or a mixture of two or more of these metals such as manganese and cobalt. The heavy metal component of the catalyst system may be employed in an elemental, combined or ionic form. Cobalt and manganese are the preferred heavy metals, with cobalt being especially preferred. The cobalt may be supplied in the form of an organic acid salt or other compound which is soluble in the solvent employed. Bromine may also be supplied in an elemental, combined or ionic form. Sources other than bromine itself include ammonium bromide, potassium bromide, hydrogen bromide, tetrabromomethane, benzyl bromide and other bromine-containing compounds which are soluble in the solvent employed in the process. An especially preferred catalyst system is a homogeneous mixture of cobalt and bromide dissolved in a reaction medium or solvent which is relatively pure acetic acid. The concentration of cobalt in the liquid-phase effluent stream of the oxidation zone should be above about 10 wt. ppm. expressed as elemental cobalt. Other suitable oxidation catalyst systems may however be used in the oxidation zone.

The oxygen consumed in the oxidation zone is preferably supplied in a vapor stream which is first admixed with the aromatic hydrocarbon in the oxidation zone. The required oxygen may be supplied in the form of essentially pure oxygen or as part of an oxygen-containing gas stream such as air. Air which has been enriched with oxygen or admixed with ozone may also be used. The rate at which the oxygen is charged to the oxidation zone should be carefully monitored to prevent the oxygen concentration in the gas at the top of the oxidation zone and at points downstream including the condenser, etc., from reaching the explosive limit, which is often specified as about 8 percent.

The vapor-phase oxidation zone effluent stream is partially condensed and is then separated into vapor and liquid streams. The uncondensed vapor, referred to herein as the oxidation zone off-gas stream, is passed into a first scrubbing zone wherein it is contacted with a water stream at conditions effective to cause the water stream to absorb or take up essentially all of the acetic acid, methyl acetate and other volatile water-soluble hydrocarbons in the vapor stream. As used herein, the term "essentially all" is intended to indicate at least 95 mole percent of the chemical referred to. The elevated pressure maintained in the oxidation zone allows the expenditure of a sizable amount of energy to effect the desired intimate contact of the off-gas stream with the water. The initial portion of this scrubbing or contacting step may therefore be effected in a venturi. The scrubbing zones preferably comprise vertical trayed scrubber columns containing about 10 to 15 horizontal sieve trays.

The oxidation zone off-gas stream is preferably scrubbed in a different zone than the vapor streams removed from the acetic acid and methyl acetate fractionation zones. It is also preferred that the oxidation zone off-gas stream is contacted with water at an elevated pressure greater than that used in these fractionation zones and which is not greatly reduced from that maintained in the oxidation zone. Conventional countercurrent contacting of the vapors with the water streams is adequate. Both of the scrubbing zones may be operated at temperatures in the broad range of from about 10° to about 45° C. A pressure of from about 2.0 to about 10 atm. absolute may be employed in the first scrubbing zone, and the second scrubbing zone is preferably operated at a positive pressure below 2.0 atm. absolute.

Normally all of the acetic acid-rich mother liquor stream produced in the crystal recovery zone is recycled to the oxidation zone. This stream is formed by the admixture of essentially all of the liquid in the liquid-phase oxidation zone effluent stream with acetic acid used as the washing liquid. A small portion of the mother liquor stream may be passed into a vaporization zone which preferably comprises a vertical cylindrical vessel. A liquid-vapor interface is maintained in a lower one-half of the vessel, with the retained liquid being heated by a suitable source. An external thermo-syphon reboiler operated on temperature control may be employed. Steam having a pressure of about 11 atm. g. may be used as a heating medium. A pressure of from about 1.2 to about 8.0 atm. may be employed in the vaporization zone. The temperature of the liquid within the vaporization zone will be set by the composition of the liquid and the pressure imposed. The function of the vaporization zone is the removal of heavy reaction by-products which gradually accumulate in the mother liquor stream.

A suitable acetic acid fractionation zone comprises a single multi-tray column. Titanium or other corrosion-resistant metals should be employed. The acetic acid fractionation zone is preferably operated at a pressure of from about 1.0 to 2.5 atm. absolute and at the bottoms temperature necessary to provide good fractionation at the imposed pressure. Representative bottoms conditions include a temperature of about 130° C. to 140° C. at approximately 1.8 atm. abs. Overhead vapor temperatures corresponding to these sets of conditions may vary between approximately 78° C. and 105° C. The overhead vapors should be condensed to the maximum extent practical. The net vapor stream removed from the overhead system of the acetic acid fractionation zone should be at a temperature below 60° C. and preferably below 40° C. to minimize the acetic acid and methyl acetate content of the vapor stream.

The methyl acetate fractionation zone preferably comprises a single multi-tray column. The methyl acetate fractionation zone is also preferably operated at a pressure of from about 1.0 to 2.5 atm. absolute. Unless otherwise specified, all fractionation conditions listed herein refer to conditions at the top of the respective column. The methyl acetate fractionation zone may be operated with a bottoms liquid temperature of 116° C. at a bottoms pressure of about 1.5 atm. absolute. The overhead vapor stream of this zone should be cooled to a temperature below approximately 50° C. in the overhead condenser. The net vapor stream removed from the overhead system of the methyl acetate column is passed into the second scrubbing zone. The net overhead liquid removed from the methyl acetate fractionation column will be a mixture of water and methyl acetate due to the formation of an acetate-rich azeotrope.

The preferred embodiment of the invention may be characterized as a process for the production of terephthalic acid by the oxidation of a p-xylene which comprises the steps of passing into a catalytic liquid-phase oxidation zone operated at oxidation-promoting conditions a feed stream comprising p-xylene, hereinafter described first and second recycle liquid streams and a first vapor stream comprising oxygen, effecting the oxidation of p-xylene and the production of a liquid-phase oxidation zone effluent stream comprising a terephthalic acid, water, acetic acid and oxidation zone by-products and a vapor-phase oxidation zone effluent stream comprising acetic acid, methyl acetate and nitrogen; passing the liquid-phase oxidation zone effluent stream into a crystal recovery zone wherein crystals of terephthalic acid are recovered from the liquid-phase oxidation zone effluent stream and the crystals are then contacted with a washing liquid stream comprising acetic acid to produce a mother liquor stream comprising acetic acid, water and oxidation zone by-products and a crystal stream comprising terephthalic acid crystals; passing the crystal stream through a drying zone to produce a product comprising the terephthalic acid; passing at least a first portion of the mother liquor stream into the oxidation zone as the first recycle liquid stream; partially condensing the vapor-phase oxidation zone effluent stream and then separating the resultant liquid and vapor phases into a condensate liquid stream comprising water, methyl acetate and acetic acid and an oxidation zone off-gas stream comprising acetic acid, methyl acetate and nitrogen; returning a first portion of the condensate liquid stream to the oxidation zone as the previously referred to second recycle liquid stream; passing a second portion of the condensate liquid stream into an acetic acid fractionation zone operated at conditions effective to produce a first overhead vapor stream comprising water and a first bottoms liquid stream comprising acetic acid; passing at least a portion of the first bottoms liquid stream into the crystal recovery zone as the previously referred to washing liquid stream; passing the oxidation zone off-gas stream into a first scrubbing zone and therein contacting the oxidation zone off-gas stream with a first water stream at scrubbing conditions effective to transfer acetic acid and methyl acetate from the oxidation zone off-gas stream to the first water stream and thereby forming a first vent gas stream comprising oxygen and a first scrubbing zone liquid stream comprising water and acetic acid; passing the first scrubbing zone liquid stream into the acetic acid fractionation zone; passing the first overhead vapor stream through a first overhead condenser and thereby forming a first overhead liquid comprising water and methyl acetate and which is collected in a first overhead receiver; withdrawing a first overhead liquid stream from the first overhead receiver, passing a first portion of the first overhead liquid stream into the acetic acid fractionation zone as reflux liquid and passing a second portion of the first overhead liquid stream into an intermediate locus of a methyl acetate fractionation zone operated at conditions effective to form a second overhead vapor stream comprising methyl acetate and a second bottoms liquid stream comprising water and substantially free of methyl acetate and acetic acid; passing the second overhead vapor stream through a second overhead condenser and thereby forming a second overhead liquid comprising methyl acetate and which is collected in a second overhead receiver; withdrawing a second overhead liquid stream from the second overhead receiver, passing a first portion of the second overhead liquid stream into the methyl acetate fractionation zone as reflux liquid and removing a second portion of the second overhead stream from the process as an effluent stream; contacting a vapor stream removed from the first overhead receiver and a vapor stream removed from the second overhead receiver with a second water stream in a second scrubbing zone operated at scrubbing conditions effective to transfer methyl acetate to the second water stream and thereby forming a second vent gas stream and a second scrubbing zone liquid stream comprising water and methyl acetate; passing the second scrubbing zone liquid stream into the methyl acetate fractionation zone; and passing a first portion of the second bottoms liquid stream formed in the methyl acetate fractionation zone into the first scrubbing zone as the previously referred to first water stream and passing a second portion of the second bottoms liquid stream into the second scrubbing zone as the previously referred to second water stream.

The subject process eliminates or at least greatly reduces the environmental problems associated with the discharge of both the vapor streams and the liquid-phase water produced during the oxidation of aromatic hydrocarbons. Furthermore, the subject process is very integrated and does not require the use of chemicals or adsorbents which are not common to the oxidation process. It also does not require large amounts of equipment or equipment of experimental design. For these and other reasons, the inventive concept is very practical and provides a highly useful process for the production of benzene dicarboxylic acids.

I claim as my invention:

1. A process for the production of an aromatic carboxylic acid by the oxidation of xylene which comprises the steps of:

(a) passing into a catalytic liquid-phase oxidation zone operated at oxidation-promoting conditions a feed stream comprising xylene, hereinafter described first and second recycle liquid streams and a first vapor stream comprising oxygen, effecting the oxidation of xylene and the production of a liquid-phase oxidation zone effluent stream comprising an aromatic carboxylic acid, water, acetic acid and oxidation zone by-products and a vapor-phase oxidation zone effluent stream comprising acetic acid, methyl acetate and nitrogen;

(b) passing the liquid-phase oxidation zone effluent stream into a crystal recovery zone wherein crystals of the aromatic carboxylic acid are recovered from the liquid-phase oxidation zone effluent stream and the crystals are then contacted with a washing liquid stream comprising acetic acid to produce a mother liquor stream comprising acetic acid from the washing liquid stream, water and oxidation zone by-products and a crystal stream comprising aromatic carboxylic acid crystals;

(c) passing the crystal stream through a drying zone to produce a product comprising the aromatic carboxylic acid;

(d) passing at least a first portion of the mother liquor stream into the oxidation zone as the first recycle liquid stream;

(e) partially condensing the vapor-phase oxidation zone effluent stream and then separating the resultant liquid and vapor phases into a condensate liquid stream comprising water, methyl acetate and acetic acid and an oxidation zone off-gas stream comprising acetic acid, methyl acetate and nitrogen;

(f) passing a first portion of the condensate liquid stream into the oxidation zone as the previously referred to second recycle liquid stream;

(g) passing a second portion of the condensate liquid stream into an acetic acid fractionation zone operated at conditions effective to produce a first net overhead vapor stream comprising water and methyl acetate and a first bottoms liquid stream comprising acetic acid;

(h) passing at least a portion of the first bottoms liquid stream into the crystal recovery zone as the previously referred to washing liquid stream;

(i) passing the oxidation zone off-gas stream into a first scrubbing zone and therein contacting the oxidation zone off-gas stream with a first water stream at scrubbing conditions effective to transfer acetic acid and methyl acetate from the oxidation zone off-gas stream to the first water stream and thereby forming a first vent gas stream comprising nitrogen and a first scrubbing zone liquid stream comprising water and acetic acid;

(j) passing the first scrubbing zone liquid stream into the acetic acid fractionation zone;

(k) passing a first net overhead liquid stream from the acetic acid fractionation zone into an intermediate locus of a methyl acetate fractionation zone operated at conditions effective to form a second net overhead vapor stream comprising methyl acetate and a second bottoms liquid stream comprising water and which is substantially free of methyl acetate and acetic acid;

(l) withdrawing a second net overhead liquid stream comprising methyl acetate from the methyl acetate fractionation zone and removing the second net overhead stream from the process;

(m) contacting the first net overhead vapor stream removed from the acetic acid fractionation zone and the second net overhead vapor stream removed from the methyl acetate fractionation zone with a second water stream in a second scrubbing zone operated at scrubbing conditions effective to transfer methyl acetate to the second water stream and thereby forming a second vent gas stream and a second scrubbing zone liquid stream comprising water and methyl acetate;

(n) passing the second scrubbing zone liquid stream into the methyl acetate fractionation zone; and, (o) passing a first portion of the second bottoms liquid stream formed in the methyl acetate fractionation zone into the first scrubbing zone as the previously referred to first water stream and passing a second portion of the second bottoms liquid stream into the second scrubbing zone as the previously referred to second water stream.

2. A process for the production of an aromatic carboxylic acid by the oxidation of xylene which comprises the steps of:

(a) passing into a catalytic liquid-phase oxidation zone operated at oxidation-promoting conditions a feed stream comprising xylene, hereinafter described first and second recycle liquid streams and a first vapor stream comprising oxygen, effecting the oxidation of xylene and the production of a liquid-phase oxidation zone effluent stream comprising an aromatic carboxylic acid, water, acetic acid and oxidation zone by-products and a vapor-phase oxidation zone effluent stream comprising acetic acid, methyl acetate and nitrogen;

(b) passing the liquid-phase oxidation zone effluent stream into a crystal recovery zone wherein crystals of the aromatic carboxylic acid are recovered from the liquid-phase oxidation zone effluent stream and the crystals are then contacted with a washing liquid stream comprising acetic acid to produce a mother liquor stream comprising acetic acid, water and oxidation zone by-products and a crystal stream comprising aromatic carboxylic acid crystals;

(c) passing the crystal stream through a drying zone to produce a product comprising the aromatic carboxylic acid;

(d) passing at least a first portion of the mother liquor stream into the oxidation zone as the first recycle liquid stream;

(e) partially condensing the vapor-phase oxidation zone effluent stream and then separating the resultant liquid and vapor phases into a condensate liquid stream comprising water, methyl acetate and acetic acid and an oxidation zone off-gas stream comprising acetic acid, methyl acetate and nitrogen;

(f) passing a first portion of the condensate liquid stream into the oxidation zone as the previously referred to second recycle liquid stream;

(g) passing a second portion of the condensate liquid stream into an acetic acid fractionation zone operated at conditions effective to produce a first overhead vapor stream comprising water and methyl acetate and a first bottoms liquid stream comprising acetic acid;

(h) passing at least a portion of the first bottoms liquid stream into the crystal recovery zone as the previously referred to washing liquid stream;

(i) passing the oxidation zone off-gas stream into a first scrubbing zone and therein contacting the oxidation zone off-gas stream with a first water stream at scrubbing conditions effective to transfer acetic acid and methyl acetate from the oxidation zone off-gas stream to the first water stream and thereby forming a first vent gas stream comprising nitrogen and a first scrubbing zone liquid stream comprising water and acetic acid;

(j) passing the first scrubbing zone liquid stream into the acetic acid fractionation zone;

(k) passing the first overhead vapor stream through a first overhead condenser and thereby forming a first overhead liquid comprising water and methyl acetate and which is collected in a first overhead receiver;

(l) withdrawing a first overhead liquid stream from the first overhead receiver, passing a first portion of the first overhead liquid stream into the acetic acid fractionation zone as reflux liquid and passing a second portion of the first overhead liquid stream into an intermediate locus of a methyl acetate fractionation zone operated at conditions effective to form a second overhead vapor stream comprising methyl acetate and a second bottoms liquid stream comprising water and which is substantially free of methyl acetate and acetic acid;

(m) passing the second overhead vapor stream through a second overhead condenser and thereby forming a second overhead liquid comprising methyl acetate and which is collected in a second overhead receiver;

(n) withdrawing a second overhead liquid stream from the second overhead receiver, passing a first portion of the second overhead liquid stream into the methyl acetate fractionation zone as reflux liquid and removing a second portion of the second overhead stream from the process;

(o) contacting a vapor stream removed from the first overhead receiver and a vapor stream removed from the second overhead receiver with a second water stream in a second scrubbing zone operated at scrubbing conditions effective to transfer methyl acetate to the second water stream and thereby forming a second vent gas stream and a second scrubbing zone liquid stream comprising water and methyl acetate;

(p) passing the second scrubbing zone liquid stream into the methyl acetate fractionation zone; and, (q) passing a first portion of the second bottoms liquid stream formed in the methyl acetate fractionation zone into the first scrubbing zone as the previously referred to first water stream and passing a second portion of the second bottoms liquid stream into the second scrubbing zone as the previously referred to second water stream.

3. The process of claim 2 further characterized in that the aromatic dicarboxylic acid is terephthalic acid and the xylene is p-xylene.

4. The process of claim 2 further characterized in that the first vapor stream, the vapor-phase oxidation zone effluent stream and the oxidation zone off-gas streams comprise oxygen.

* * * * *